United States Patent
Sugisawa et al.

(10) Patent No.: US 9,549,665 B2
(45) Date of Patent: Jan. 24, 2017

(54) ENDOSCOPE

(71) Applicant: FUJIFILM Corporation, Tokyo (JP)

(72) Inventors: Tatsuya Sugisawa, Kanagawa (JP); Keisuke Naito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 103 days.

(21) Appl. No.: 14/729,670

(22) Filed: Jun. 3, 2015

(65) Prior Publication Data

US 2015/0265135 A1 Sep. 24, 2015

Related U.S. Application Data

(62) Division of application No. 13/343,916, filed on Jan. 5, 2012, now abandoned.

(30) Foreign Application Priority Data

Jan. 19, 2011 (JP) .................................. 2011-009175
Nov. 24, 2011 (JP) .................................. 2011-256771

(51) Int. Cl.
*A61B 1/00* (2006.01)
*A61B 1/005* (2006.01)
*A61B 1/015* (2006.01)

(52) U.S. Cl.
CPC ........... *A61B 1/0051* (2013.01); *A61B 1/0055* (2013.01); *A61B 1/00078* (2013.01); *A61B 1/00163* (2013.01); *A61B 1/015* (2013.01)

(58) Field of Classification Search
CPC ................................................ A61B 1/00135
(Continued)

(56) References Cited

U.S. PATENT DOCUMENTS 3,699,950 A * 10/1972 Humphrey, Jr. .... A61B 1/00117
285/114
4,327,711 A * 5/1982 Takagi ............... A61B 1/00071
600/139
(Continued)

FOREIGN PATENT DOCUMENTS

EP 1 011 388 A1 4/2008
JP 58-117602 U 8/1983
(Continued)

OTHER PUBLICATIONS

US 5,704,359, 01/1998, Milo (withdrawn)
(Continued)

*Primary Examiner* — Anhtuan T Nguyen
*Assistant Examiner* — Jae Woo
(74) *Attorney, Agent, or Firm* — Birch, Stewart, Kolasch & Birch, LLP

(57) ABSTRACT

There is provided an endoscope that prevents occurrence of buckling of a flexible body built in an insertion part of the endoscope without damaging other built-in components, and is easy to manufacture without impairing the curving manipulability. The endoscope includes a curvable portion, and an elongated insertion part being inserted into a subject. The endoscope has an elongated flexible body built in the insertion part, and a flexible protective tube that covers an outer periphery of the flexible body. The protective tube has a first region that covers the range of the flexible body, and a second region that covers the range of the soft portion. The elastic constant of the first region is smaller than the elastic constant of the second region, and the external diameter of the protective tube in the first region is larger than the external diameter of the protective tube of the second region.

2 Claims, 12 Drawing Sheets

(58) Field of Classification Search
USPC . 600/123, 139, 141, 142, 144, 182; 604/525
See application file for complete search history.

(56) References Cited

U.S. PATENT DOCUMENTS

| | | | | |
|---|---|---|---|---|
| 4,347,837 A * | 9/1982 | Hosono | G02B 23/2476 | 356/241.4 |
| 4,353,358 A * | 10/1982 | Emerson | A61B 1/0056 | 600/139 |
| 4,577,621 A * | 3/1986 | Patel | A61B 1/00156 | 600/114 |
| 4,580,551 A * | 4/1986 | Siegmund | A61B 1/0055 | 600/139 |
| 4,771,766 A * | 9/1988 | Aoshiro | A61B 1/121 | 600/155 |
| 4,805,596 A * | 2/1989 | Hatori | A61B 1/0057 | 600/139 |
| 4,879,991 A * | 11/1989 | Ogiu | A61B 1/05 | 600/110 |
| 4,881,810 A * | 11/1989 | Hasegawa | A61B 1/00101 | 356/241.5 |
| 4,919,114 A * | 4/1990 | Miyazaki | A61B 1/00183 | 348/65 |
| 5,025,778 A * | 6/1991 | Silverstein | A61B 1/0008 | 600/104 |
| 5,083,549 A | 1/1992 | Cho et al. | | |
| 5,217,002 A * | 6/1993 | Katsurada | A61B 1/00071 | 600/139 |
| 5,235,964 A * | 8/1993 | Abenaim | A61B 1/0055 | 600/139 |
| 5,301,061 A * | 4/1994 | Nakada | A61B 1/00059 | 348/75 |
| 5,448,988 A * | 9/1995 | Watanabe | A61B 1/0055 | 138/118 |
| 5,465,710 A * | 11/1995 | Miyagi | A61B 1/0055 | 138/123 |
| 5,476,090 A * | 12/1995 | Kishi | A61B 1/00135 | 600/121 |
| 5,483,951 A * | 1/1996 | Frassica | A61B 1/00142 | 600/104 |
| 5,529,820 A * | 6/1996 | Nomi | A61L 29/041 | 428/36.4 |
| 5,536,235 A * | 7/1996 | Yabe | A61B 1/00071 | 138/118 |
| 5,586,968 A * | 12/1996 | Grundl | A61B 1/00151 | 600/114 |
| 5,591,120 A * | 1/1997 | Machida | A61B 1/00135 | 138/120 |
| 5,704,899 A * | 1/1998 | Milo | A61B 1/0056 | 385/107 |
| 5,938,587 A * | 8/1999 | Taylor | A61B 1/018 | 138/118 |
| 5,976,074 A * | 11/1999 | Moriyama | A61B 1/00078 | 600/139 |
| 6,171,235 B1 * | 1/2001 | Konstorum | A61B 1/0008 | 600/121 |
| 6,174,280 B1 * | 1/2001 | Oneda | A61B 1/00078 | 600/114 |
| 6,179,776 B1 * | 1/2001 | Adams | A61B 1/00073 | 600/121 |
| 6,328,731 B1 * | 12/2001 | Ouchi | A61B 10/06 | 600/121 |
| 6,464,632 B1 * | 10/2002 | Taylor | A61B 1/005 | 138/174 |
| 6,485,411 B1 * | 11/2002 | Konstorum | A61B 1/0058 | 600/139 |
| 6,599,239 B2 * | 7/2003 | Hayakawa | A61B 1/00071 | 600/139 |
| 6,723,063 B1 * | 4/2004 | Zhang | A61B 1/00135 | 604/22 |
| 6,814,697 B2 * | 11/2004 | Ouchi | A61B 1/00135 | 600/121 |
| 6,852,078 B2 * | 2/2005 | Ouchi | A61B 1/00135 | 600/121 |
| 6,921,363 B2 * | 7/2005 | Knowles | A61B 8/12 | 600/139 |
| 7,169,105 B2 * | 1/2007 | Iwasaka | A61B 1/00071 | 600/139 |
| 7,341,554 B2 * | 3/2008 | Sekine | A61B 1/00135 | 600/106 |
| 2002/0143237 A1 * | 10/2002 | Oneda | A61B 1/00082 | 600/116 |
| 2004/0193013 A1 | 9/2004 | Iwasaka et al. | | |
| 2005/0277809 A1 * | 12/2005 | Takano | A61B 1/00082 | 600/114 |
| 2006/0258906 A1 * | 11/2006 | Binmoeller | A61B 1/00135 | 600/114 |
| 2007/0015965 A1 * | 1/2007 | Cox | A61B 1/00082 | 600/114 |
| 2007/0112250 A1 * | 5/2007 | Kura | A61B 1/00135 | 600/114 |
| 2007/0203393 A1 * | 8/2007 | Stefanchik | A61B 1/00073 | 600/106 |
| 2008/0183033 A1 * | 7/2008 | Bern | A61B 1/0016 | 600/101 |
| 2009/0069632 A1 * | 3/2009 | McIntyre | A61B 1/00098 | 600/146 |
| 2009/0299352 A1 * | 12/2009 | Zerfas | A61B 1/00165 | 606/15 |
| 2010/0076265 A1 | 3/2010 | Yamakawa et al. | | |
| 2015/0272424 A1 * | 10/2015 | Abe | B29C 47/0026 | 600/140 |

FOREIGN PATENT DOCUMENTS

| | | |
|---|---|---|
| JP | 59-30504 A | 2/1984 |
| JP | 5-323210 A | 12/1993 |
| JP | 7-181397 A | 7/1995 |
| JP | 2001-70230 A | 3/2001 |
| JP | 2004-089265 A | 3/2004 |
| JP | 2007-37649 A | 2/2007 |
| JP | 2009-247727 A | 10/2009 |

OTHER PUBLICATIONS

Extended European Search Report, dated May 15, 2012, in related application No. EP11196045.6.

Japanese Office Action, dated Jan. 22, 2013, in related application No. JP2011-256771.

* cited by examiner

ENDOSCOPE

BACKGROUND OF THE INVENTION

This application is a Divisional of copending application Ser. No. 13/343,916, filed on Jan. 5, 2012, which claims priority under 35 U.S.C. §119(a) to Application No. JP2011-009175, filed in Japan on Jan. 19, 2011 and to Application No. JP2011-256771, filed in Japan on Nov. 24, 2011, all of which are hereby expressly incorporated by reference into the present application.

FIELD OF THE PRESENT INVENTION

The present invention relates to an endoscope including a curvable portion.

DESCRIPTION OF THE RELATED ART

Endoscopes widely used for medical and industrial uses have an insertion part to be inserted into a subject (into a body cavity), and a manipulating part that is manipulated by an operator, and built-in components, such as optical fibers for illumination, forceps channel through which a treatment tool is inserted, an air supply and water supply channel are arranged in the insertion part. Moreover, a curvable portion that is operated to curve is provided at the distal end of the insertion part, and the curvable portion can be curved up and down and right and left in conjunction with angle knobs of the manipulating part (for example, refer to JP 2007-37649A).

These built-in components, such as optical fibers, are flexible bodies that are apt to curve. JP 2007-37649A describes a configuration in which a flexible body to be bent is protected by densely and spirally winding an element wire having predetermined elasticity around an outer periphery of a flexible body that is a built-in component to form a regulating part in which adjacent element wires are bonded and fixed to each other. In this endoscope, the regulating part is arranged particularly in the region of the curvable portion that is apt to bend in the flexible body to prevent occurrence of buckling or decrease in lifespan.

SUMMARY OF THE INVENTION

However, in the configuration in which the element wire is densely and spirally wound on the outer periphery of the flexible body, the manufacturing process becomes complicated and the costs become high. Additionally, since a level difference caused by the element wires occurs outside the flexible body, and the surface of the element wire is hard, other built-in components are apt to be damaged. Moreover, when the element wire that is densely and spirally wound is unwound from the outer periphery of the flexible body, there is a concern that other built-in components may be damaged or the element wire may catch. Additionally, since the diameter of the flexible body is increased due to the spiral element wire, this configuration is disadvantageous to reducing the diameter of the insertion part. Moreover, in the case of an endoscope of a type in which a blue laser beam from a laser light source and green to yellow excitation light components obtained by wavelength conversion with fluorescent bodies are synthesized to generate white light, a single mode fiber (for example, optical fiber) with a diameter which is reduced to about 0.3 mm is used the flexible body. If the flexible body with the reduced diameter is used, the durability of the flexible body is not sufficiently secured due to the reduction in diameter, and the flexible body is apt to be damaged due to buckling or bending of the flexible body when the endoscope is manufactured and when the endoscope is used.

The present invention has been made in view of the above-mentioned problems and an object of the present invention is to provide an endoscope that prevents a flexible body with a reduced diameter, such as an optical fiber, which is built in an insertion part of the endoscope, from being damaged due to buckling, bending, or the like, without damaging other built-in components, and is easy to manufacture without impairing the curving manipulability of a curvable portion.

The present invention has the following configuration. An endoscope including a curvable portion provided to extend at a distal end of a soft portion having flexibility, an elongated insertion part to be inserted into a subject, an elongated flexible body built in the insertion part, and a flexible protective tube that covers an outer periphery of the flexible body, the protective tube having a first region that covers the flexible body located at least in the curvable portion, and a second region that covers the flexible body located in the soft portion, and the elastic constant of the first region being smaller than the elastic constant of the second region, and the external diameter of the protective tube in the first region being larger than the external diameter of the protective tube of the second region.

In the endoscope of the present invention, the flexible body that is built in the insertion part of the endoscope and is covered with the protective tube in which the elastic constant of the protective tube located at least in the curvable portion is smaller than the elastic constant of the protective tube located in the soft portion, and the external diameter of the protective tube in the first region is larger than the external diameter of the protective tube of the second region, so that this flexible body does not undergo any damage, and the buckling of the flexible body can be prevented without damaging other built-in components. Moreover, since the elastic constant of the protective tube of the curvable portion is small, the required torque for the curving manipulation of the curvable portion is suppressed to be small. Since the flexible body covered with the protective tube can be smoothly put into the insertion part during manufacture, the assemblability when the endoscope is manufactured improves.

BRIEF DESCRIPTION OF THE DRAWINGS

FIG. 9B is a schematic explanatory view showing a configuration in which the connection part is provided at an axially different position that is different for each light guide.

DESCRIPTION OF THE PREFERRED EMBODIMENTS

An embodiment of the present invention will be described in detail with reference to the accompanying drawings.

Figure 1:
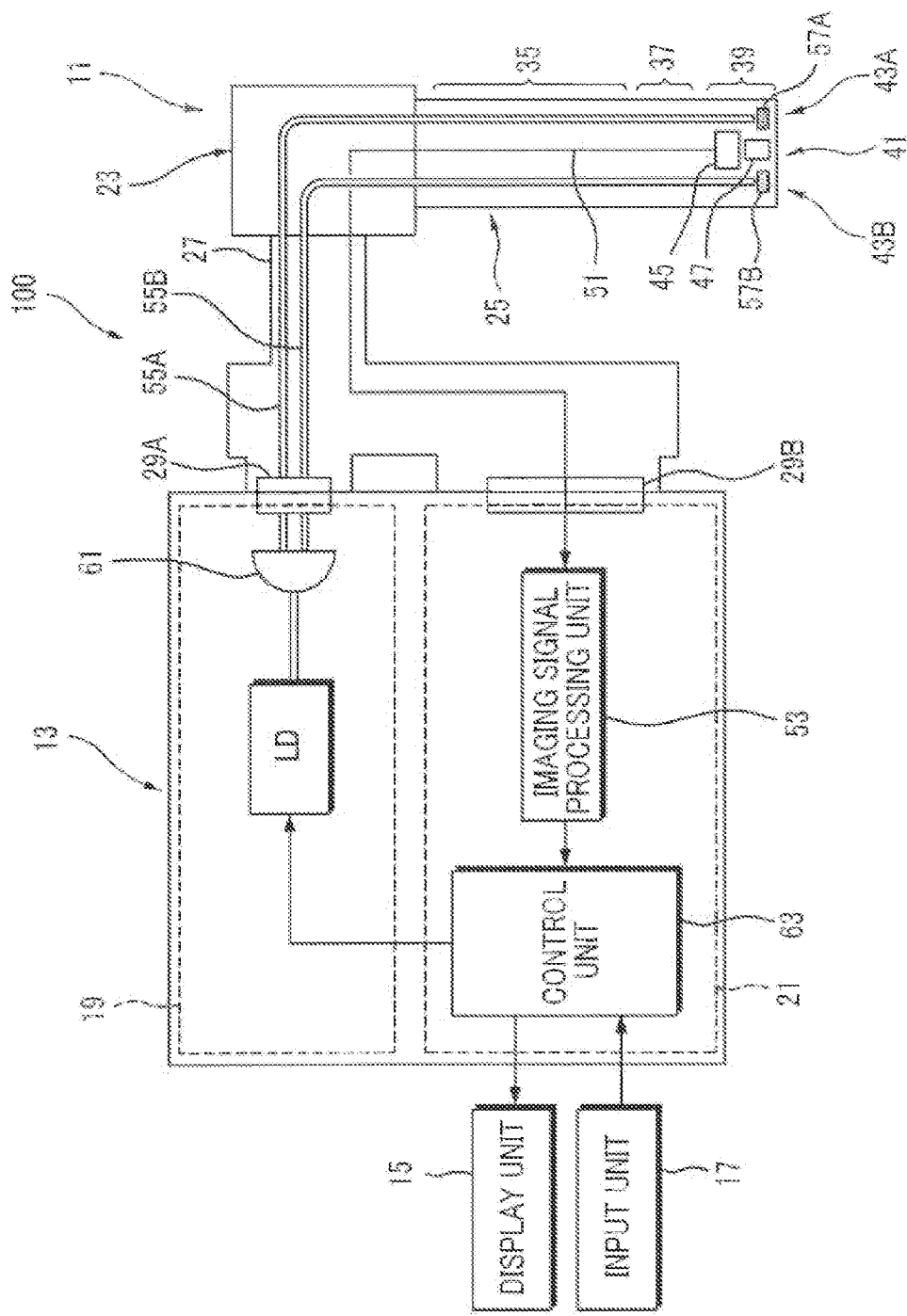
FIG. 1 is a view illustrating an embodiment of the present invention, and a configuration diagram of an endoscope apparatus showing an endoscope and respective devices to which the endoscope is connected.
Figure 2:
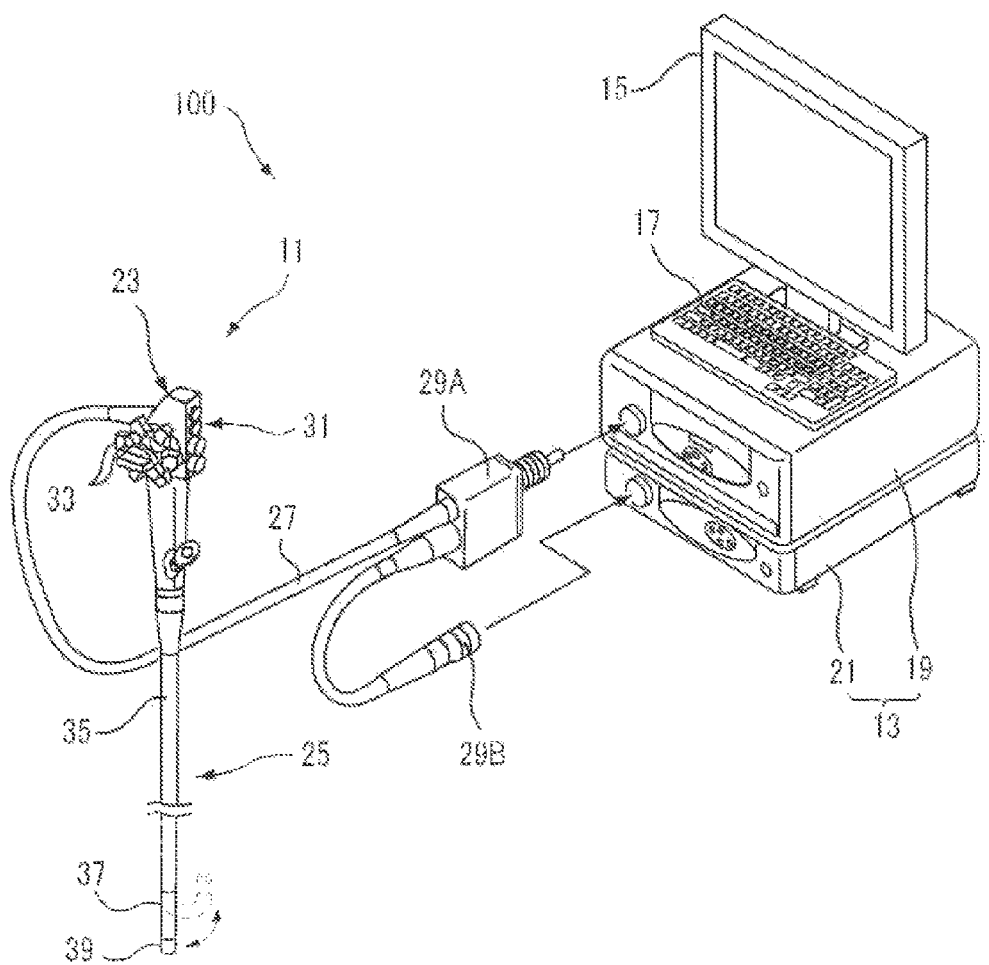
FIG. 2 is an external view showing a specific configuration example of the endoscope apparatus.

FIG. 1 is a view illustrating the embodiment of the present invention, and a configuration diagram of an endoscope apparatus showing an endoscope and respective devices to which the endoscope is connected, and FIG. 2 is an external view showing a specific configuration example of the endoscope apparatus.

The endoscope apparatus 100, as shown in FIG. 1, includes an endoscope 11, a control device 13, a display unit 15, such as a monitor, and an input unit 17, such as a keyboard or a mouse through which information is input to the control device 13. The control device 13 has a light source device 19 and a processor 21 that performs signal processing of a captured image.

The endoscope 11 includes a body manipulating part 23 and an elongated insertion part 25 connected to the body manipulating part 23 and inserted into a subject (body cavity). A universal cord 27 is connected to the body manipulating part 23, and a distal end of the universal cord 27 is connected with the light source device 19 via a light guide (LG) connector 29A, and is connected to the processor 21 via a video connector 29B.

As shown in FIG. 2, in the body manipulating part 23 of the endoscope 11, various manipulation buttons 31, such as buttons for carrying out suction, air supply, and water supply at the distal end of the insertion part 25, and a shutter button during imaging, are installed together, and a pair of angle knobs 33 is provided.

The insertion part 25 is constituted by a soft portion 35, a curvable portion 37, and a distal end portion (endoscope distal end portion) 39 sequentially from the body manipulating part 23 arranged at a proximal end. The curvable portion 37 is remotely curved by turning the angle knobs 33 of the body manipulating part 23, so that the distal end portion 39 is directed to a desired direction.

As shown in FIG. 1, an observation window 41 of an imaging optical system and illumination windows 43A and 43B of an illumination optical system are arranged at the endoscope distal end portion 39. Reflected light from a subject caused by illumination light radiated from the respective illumination windows 43A and 43B is imaged by an imaging device 45 through the observation window 41. The imaged observation image is displayed on the display unit 15 connected to the processor 21.

The imaging optical system has the imaging device 45, such as a CCD (Charge Coupled Device) type image sensor or a CMOS (Complementary Metal Oxide Semiconductor) type image sensor, and an optical member 47, such as a lens that forms an observation image on the imaging device 45. The observation image that is formed on a light-receiving plane of the imaging device 45 and is fetched, is converted into electrical signals, and the converted image signals are input to an imaging signal processing unit 53 of the processor 21 through a signal cable 51, and are converted into video signals in the imaging signal processing unit 53.

The processor 21 includes a control unit 63, and an imaging signal processing unit 53 that generates video signals. The control unit 63 performs proper image processing on image data of the observation image output from the imaging signal processing unit 53, and makes the image-processed image data projected on the display unit 15. Additionally, a driving signal is output to a laser light source LD of the light source device 19 so as to make illumination light with a desired light quantity be emitted from the respective illumination windows 43A and 43B. The control unit 63 is connected to networks, such as a LAN (not shown), to control the overall endoscope apparatus 100, such as distributing information including image data.

The illumination optical system has the light source device 19, a pair of optical fibers 55A and 55B connected to the light source device 19 via the connector 29A, and wavelength converting members 57A and 57B respectively arranged at light emission ends of the optical fibers 55A and 55B. The light source device 19 has a laser light source LD that is a semiconductor light-emitting element, and the optical coupler 61 that branches the emission light from laser light source LD, and introduces the branched emission light into the respective optical fibers 55A and 55B.

The laser light source LD is a semiconductor laser that emits blue light with a central wavelength of 445 nm, for example, a broad area type InGaN-based laser diode can be used. Additionally, the laser light source LD may be constituted by a plurality of laser light sources, for example, may be combined with a semiconductor laser that emits purple light with a central wavelength of 405 nm so as to make light be selectively output from each laser light source.

Figure 3:
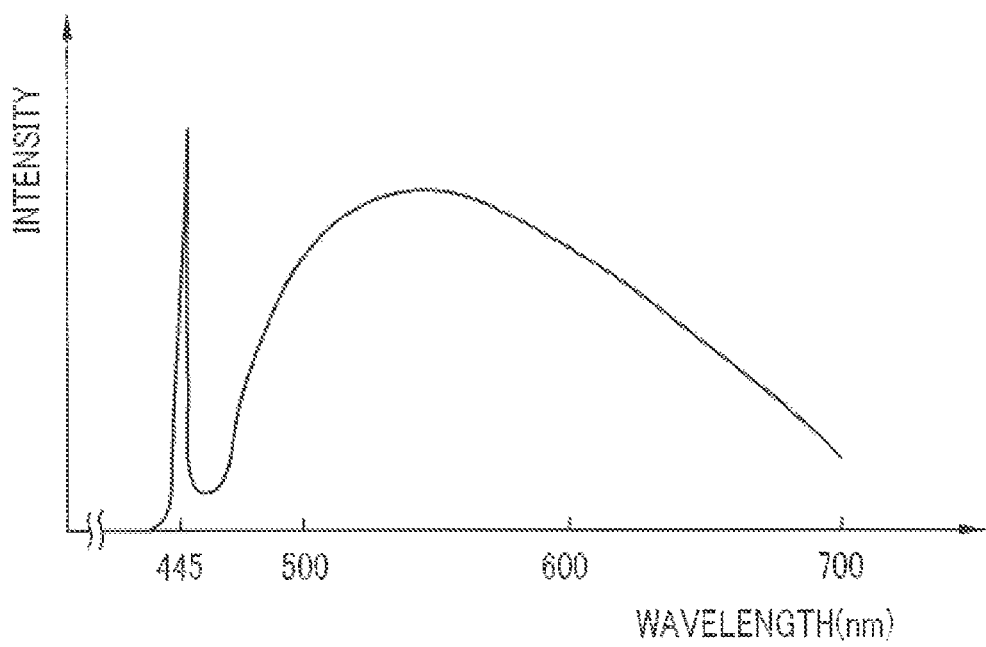
FIG. 3 is a graph showing spectral characteristics of emission light.

The wavelength converting members 57A and 57B include a plurality of kinds of fluorescent bodies (for example, fluorescent bodies or the like including a YAG-based fluorescent body or BAM ($BaMgAl_{10}O_{37}$)), which adsorb a portion of a blue laser beam output from the laser light source LD and are excited in green to yellow to emit light. The blue laser beam from the laser light source LD and the green excitation to yellow excitation light that are obtained by converting the wavelength of this blue laser beam are synthesized to generate white light by the wavelength converting members 57A and 57B so as to show spectral characteristics of emission light in FIG. 3.

The control unit 63 of the processor 21 controls the light quantity of the laser light source LD to make a laser beam output from the laser light source LD. The output laser beam is introduced into the respective optical fibers 55A and 55B, and is guided to the endoscope distal end portion 39. The laser beam guided to the optical fibers 55A and 55B is irradiated to the wavelength converting members 57A and 57B, and thereby, white illumination light is emitted from the illumination windows 43A and 43B.

Figure 4:
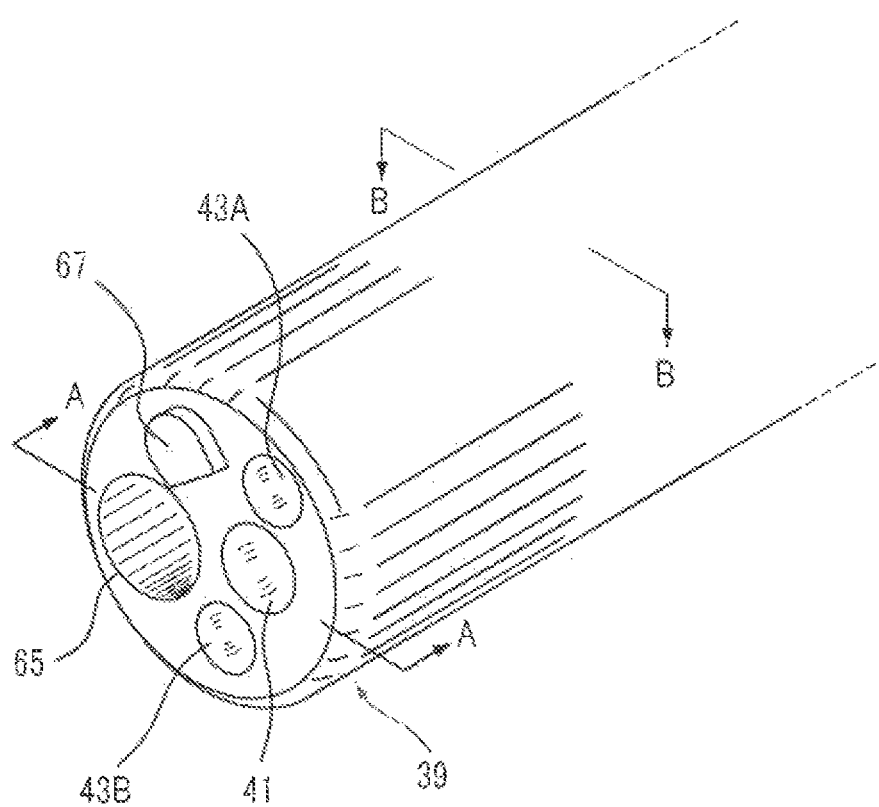
FIG. 4 is a perspective view of an endoscope distal end portion.
Figure 5:
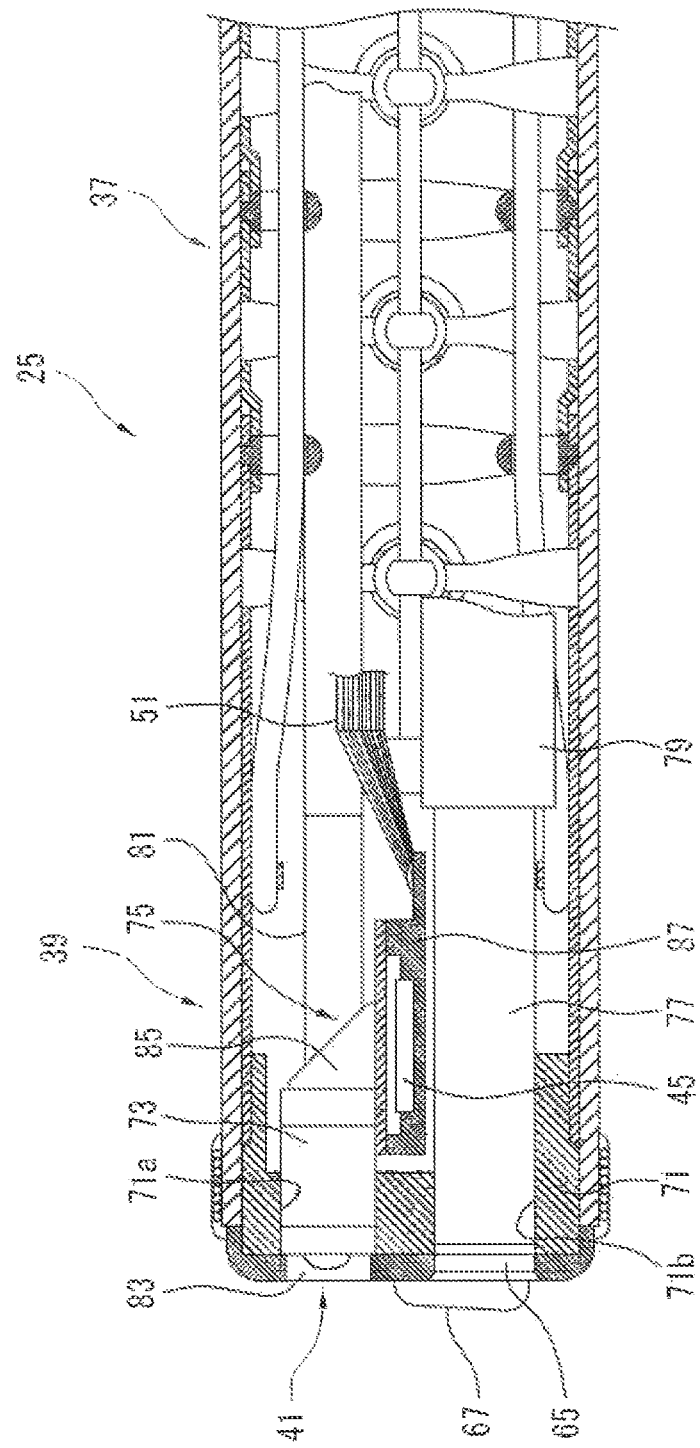
FIG. 5 is a schematic cross-sectional configuration diagram in a cross-section A-A of FIG. 4.
Figure 6:
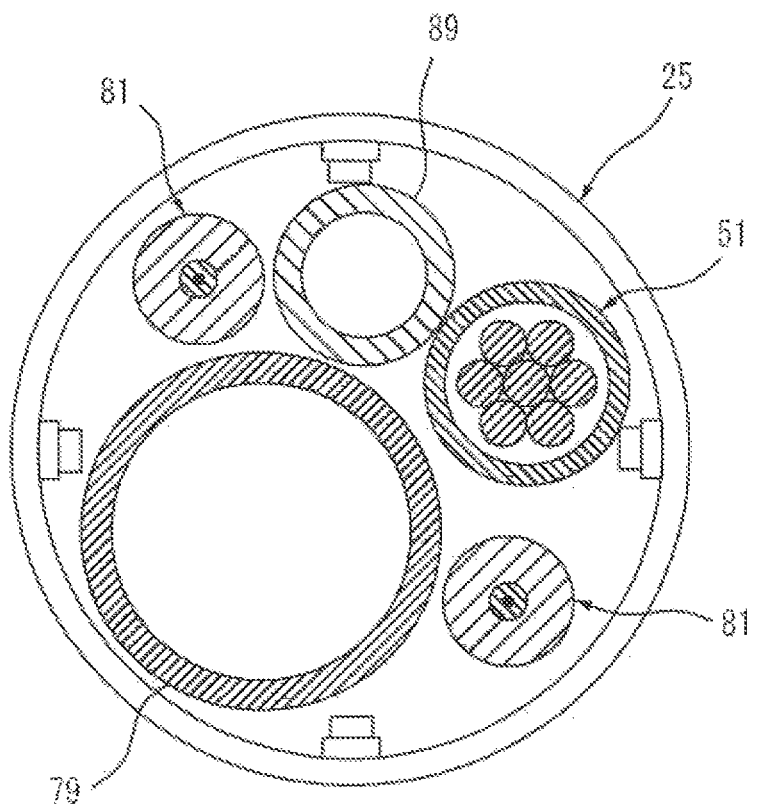
FIG. 6 is a schematic cross-sectional configuration diagram in a cross-section B-B of FIG. 4.

FIG. 4 is an external perspective view of the endoscope distal end portion 39, FIG. 5 is a schematic cross-sectional configuration diagram in a cross-section A-A of FIG. 4, and FIG. 6 is a schematic cross-sectional configuration diagram in a cross-section B-B of FIG. 4.

As shown in FIG. 4, the above-mentioned observation window 41 for observing a subject, and the illumination windows 43A and 43B that emit illumination light are arranged at the endoscope distal end portion 39, and the illumination windows 43A and 43B are arranged on both sides of the observation window 41. Additionally, a forceps opening 65 through which various kinds of forceps are inserted, an air supply and water supply nozzle 67 that supplies air and supplies water toward the observation window 41 are arranged at the endoscope distal end portion 39.

As shown in a cross-sectional configuration of FIG. 5, a distal end hard portion 71 made of a metallic material, such as a stainless steel material, an imaging unit 75 fixed by fitting a lens barrel 73 into a bored hole 71a formed in the distal end hard portion 71, a forceps pipe 77 disposed in a different bored hole 71b, a forceps tube 79 made of a soft material connected to the metal forceps pipe 77, a light guide unit 81 of the illumination optical system, and the like are arranged at the endoscope distal end portion 39.

The imaging unit 75 includes the lens barrel 73 in which an objective lens 83 that becomes the observation window 41 is accommodated, a prism 85 that changes the direction of light fetched from the lens barrel 73 at right angles, and the imaging device 45 that forms the light fetched via the prism 85 mounted on a circuit board 87 as an image to generate image signals. As mentioned above, the image information output from the imaging device 45 is transmitted to the imaging signal processing unit 53 of the processor 21 (refer to FIG. 1) via the signal cable 51, and is processed into an image for display.

The above light guide unit 81 and the signal cable 51, as shown in FIG. 6, are built in along the axial direction of the endoscope insertion part 25 along with to the forceps tube 79 or the air supply and water supply tube 89 connected to the air supply and water supply nozzle 67 (refer to FIGS. 4 and 5).

Here, the light guide unit 81 in which the illumination windows 43A and 43B of the illumination optical system, the wavelength converting members 57A and 57B, and the optical fibers 55A and 55B are integrally formed will be described.

Figure 7:
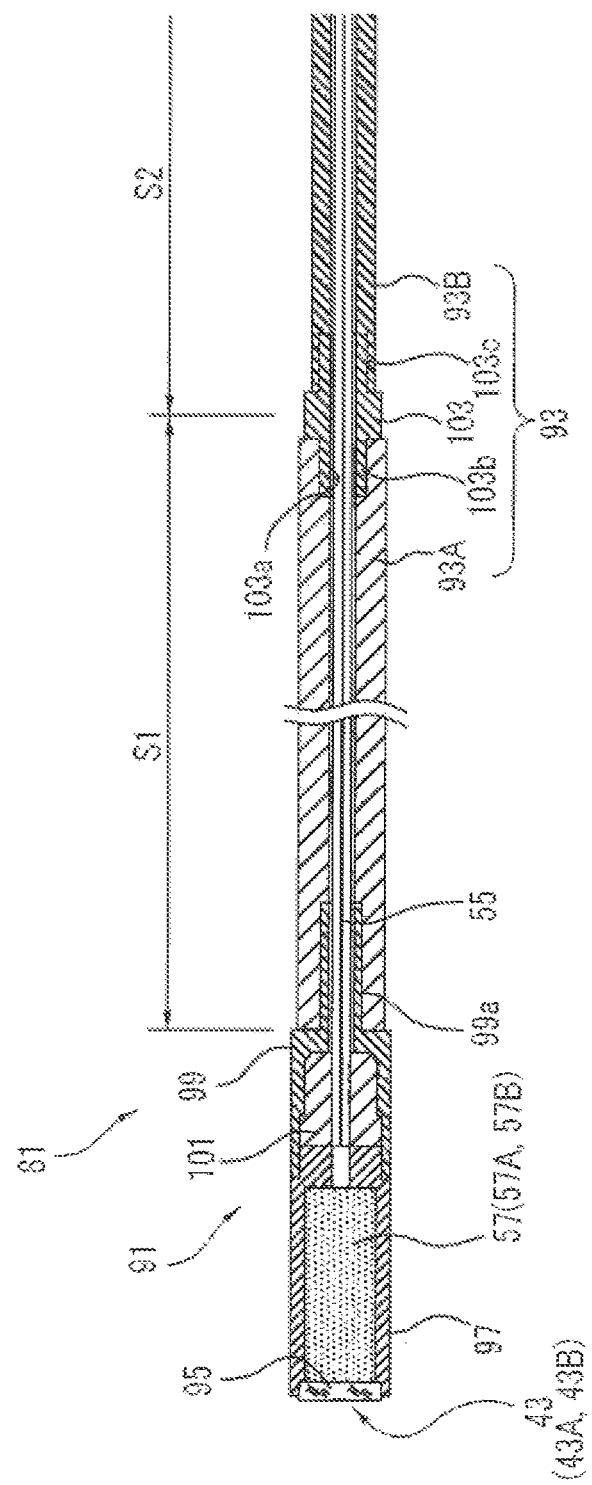
FIG. 7 is a configuration diagram of a light guide unit.

As shown in FIG. 7, the light guide unit 81 has a distal end light-projecting portion 91, an optical fiber 55 (55A, 55B) that is a flexible body of which a light emission end is connected to the distal end light-projecting portion 91, and a protective tube 93 that covers the outer periphery of the optical fiber 55.

The distal end light-projecting portion 91 has a cylindrical distal end sleeve 97 one face of which is blocked by a light-projecting plate 95 that becomes an illumination window 43 (43A, 43B), a wavelength converting member 57 (57A, 57B) that is arranged in the distal end sleeve 97, a coupling member 99 that couples the distal end side of the protective tube 93 and the proximal end side of the distal end sleeve 97 together, and a ferrule 101 that is arranged inside the coupling member 99 to support the optical fiber 55.

The protective cube 93 has a first protective tube 93A, a second protective tube 93B, and a connecting member 103 that has a central hole 103a bored therein and coaxial by connects the first protective tube 93A and second protective tube 93B together. The optical fiber 55 is inserted into the internal space of each of the protective lubes 93A and 93B.

Here, Not bending the optical fiber to the bending limit radius (0.85 mm) or less of the optical fiber 55 is needed so as for the optical fiber 55 extending in the curvable portion 37 not to cause disconnection due to buckling by virtue of curving of the curvable portion 37. That is, in the first protective tube 93A of the present configuration, a thickness t that can be found as ½ of the difference between the external diameter D and the internal diameter d is made larger than the greatest curvature radius $r_{max}$ at which the optical fiber 55 breaks due to bending as shown in the cross-sectional view of the first protective tube 93A in FIG. 11. Thereby, even when the protective tube 93A is bent at 180° as shown in FIG. 12, and is bent with a minimum curvature radius, the curvature radius r of the optical fiber 55 becomes always larger than the curvature radius $r_{max}$ at which breaking occurs. According to this configuration, disconnection caused by buckling does not occur in the optical fiber 55 by any manipulations of the curvable portion 37. On the other hand, since the second protective tube 93B has no necessity for carrying out curving like the curvable portion, the external diameter of the second protective tube 93B may be smaller than the external diameter D of the first protective tube 93A. In the present example, $r_{max}$=0.5 to 1.0 mm, t=0.6 to 1.5 mm, and the external diameter of the second protective tube 93B is 0.8 to 2.0 mm. As such, the external diameter of the first protective tube 93A is larger than that of the second protective tube 93B, and the external diameter from the distal end light-projecting portion 91 to the second protective tube 93B is adapted to become smaller in a stepwise fashion. Thereby, disconnection of the optical fiber can be prevented, the handlability in a single body of the light guide unit 81 becomes good, and assembling operation into the endoscope insertion part 23 becomes easy. Additionally, since the overall protective tube 93 can be formed so as to have a small diameter, reduction in the diameter of the endoscope insertion part 25 is not hindered.

Since the curvature radius of the curvable portion 37 is smaller than the curvature radius of me soft portion, the first protective tube 93A corresponding to the curvable portion 37 requires flexibility, and it is preferable that the elastic constant of the first protective tube 93A be smaller. On the other hand, since the length of the second protective tube 93B corresponding to the soft portion 35 is about 10 times larger than the length of the first protective tube 93A, if the elastic constant of the second protective tube 93B is made equal to the elastic constant of the first protective tube 93A, the elastic constants of the second protective tube 93B is insufficient, and the second protective tube 93B is apt to deflect excessively. Therefore, slidability to other members is not sufficiently secured, and the operation of assembling the second protective tube 93B into the endoscope insertion part 25 becomes difficult. For this reason, by making the elastic constant of the second protective tube 93B larger than the elastic constant of the first protective tube 93A, the optical fiber 35 can be maintained in a straight shape by the difficulty (elastic restoring force) of bending of the first protective tube 93A, and the assemblability of inserting the optical fiber 55 into the endoscope insertion part 25 improves. By making the elastic modulus of the first protective tube 93A smaller than the elastic modulus of the second protective tube 93B in this way, assemblability into the endoscope insertion part 25 can be secured while having curvability in the curvable portion 37.

The first protective tube 93A is made of a highly flexible rubber-based material, such as silicone rubber or fluorine-based rubber. The rubber-based material is chemically stable, does not deteriorate even in the case of contact with cleaning chemicals during endoscope washing, and also has little degradation with time. One end portion of the first protective tube 93A is inserted into a small-diameter connection part 99a of the coupling member 99 on the side of the distal end light-projecting portion 91, and the other end portion thereof is inserted into a small-diameter connection part 103b of the connecting member 103. In addition, the first protective tube 93A may be configured by performing fluorine-based coating on the inner peripheral surface or outer peripheral surface of the rubber-based materials or both surfaces thereof. In that case, slidability to a member coming into contact with the first protective tube 93A improves.

The second protective tube 93B is made of fluorine-based resin with excellent flexibility and slidability, such as polytetrafluoroethylene (PTFE) or a tetrafluoroethylene perfluoroalkyl vinyl ether copolymer (PFA). One end portion of the second protective tube 93B is inserted into the small-diameter connection part 103c of the connecting member 103, and the other end portion thereof is connected to the connector 29A (refer to FIG. 1).

Since the first protective tube 93A is made to have a smaller elastic constant than the second protective tube 93B, the first protective tube is more flexible than the second protective tube 93B, so that disconnection of the optical fibers 55 can be prevented. Additionally, other built-in components within the endoscope insertion part 25 are not damaged.

Since the elastic constant of the second protective tube 93B is large, attaining a reduction in diameter without reducing strength will be possible. Since the inner peripheral surface and outer peripheral surface of the second protective tube 93B have high slidability, the operation of inserting the optical fiber 55 into the tube can be reduced, and entanglement in other built-in components does not occur easily within the endoscope insertion part 25.

The above elastic constant is a parameter showing bending stiffness when each tube is macroscopically observed. The larger elastic constant shows harder bendability, and the smaller elastic constant shows easier bendability and flexibility. Specifically, the elastic constant is expressed by rigidity modulus, tensile modulus, or the like. Here, from the viewpoints of sufficiently securing the assemblability of the endoscope 11 and the curving manipulability of the curvable portion 37, and suppressing disconnection of the optical fiber 55, the tensile modulus of the first protective tube 93A is preferably in the range of 5 to 50 MPa, and the tensile modulus of the second protective tube 93B is preferably in the range of 100 to 600 MPa. If the tensile modulus is smaller than this range, the protective tube is excessively flexible, and assemblability into the endoscope insertion part 25 degrades, and if the tensile modulus is larger than this range, flexibility decreases and curvability is impaired. Additionally, the tensile modulus of the second protective tube 93B is preferably 2 to 20 times larger than the tensile modulus of the first protective tube 93A. Thereby, the curvability in the curvable portion 37 and asemblability into the endoscope insertion part 25 can be properly made compatible.

Additionally, the external diameter of the first protective tube 93A is larger than that of the second protective tube 93B, and the external diameter from the distal end light-projecting portion 91 to the second protective tube 93B is adapted to become smaller in a stepwise fashion. Thereby, the handlability in a single body of the light guide unit 81 becomes good, and assembling operation into the endoscope insertion part 25 becomes easy. Additionally since the overall protective tube 93 can be formed so as to have a small diameter, reduction in the diameter of the endoscope insertion part 25 is not hindered.

The light guide unit 81 of the above configuration and are arranged in the endoscope insertion part 25 such that a region S1 of the first protective tube 93A and a region S2 of the second protective tube 93B are made to correspond to a region of the curvable portion 37 of the endoscope insertion part 25 and a region of the soft portion 35, respectively. That is, the region S1 of the first protective tube 93A is built at least in the region of the curvable portion 37, and the region of the second protective tube 93B is built in the region of the soft portion 35.

Figure 8:
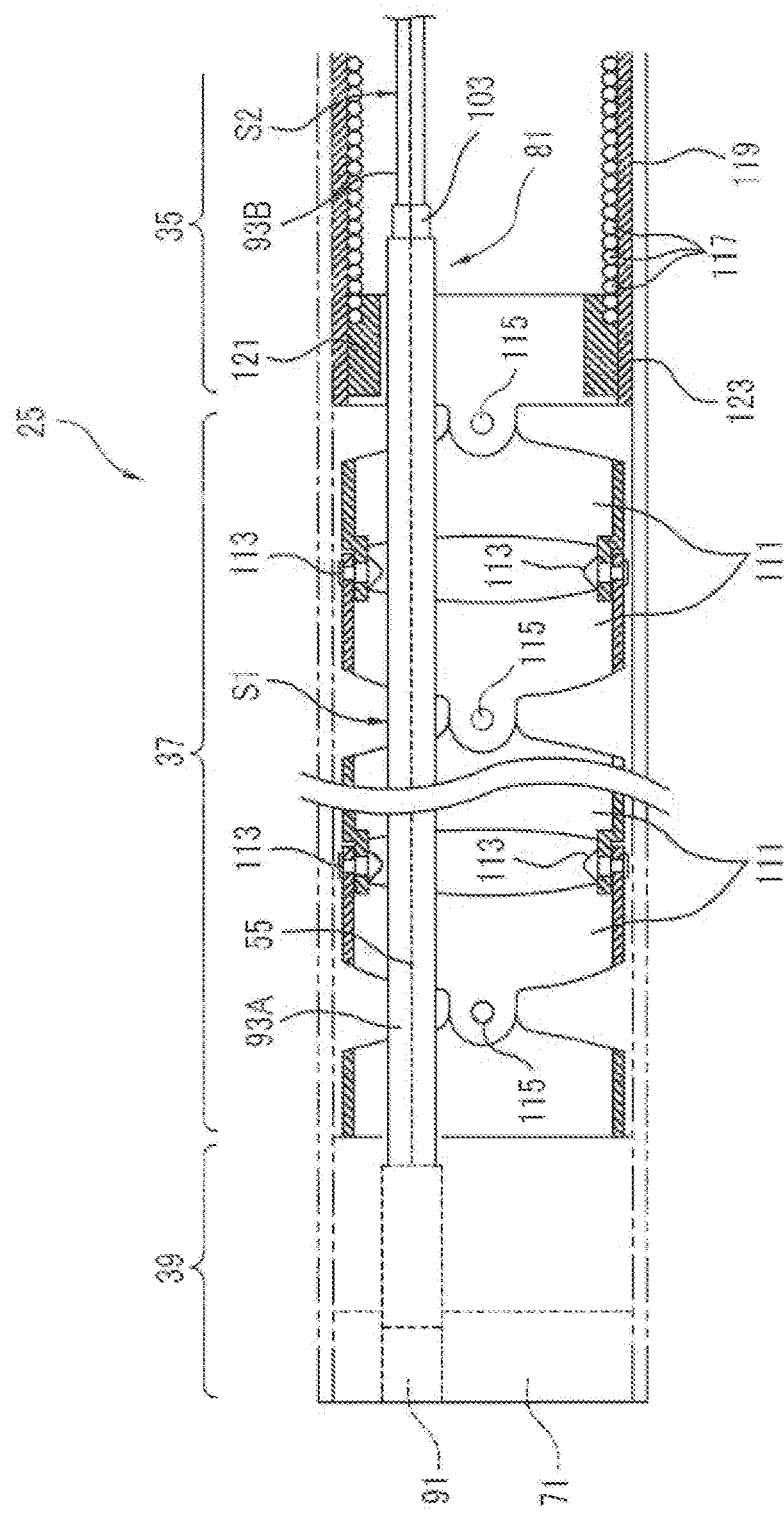
FIG. 8 is an explanatory view showing the arrangement relationship between the endoscope insertion part and the light guide unit.

An explanatory view showing the arrangement relationship between the endoscope insertion part and the light guide unit is shown in FIG. 8. The light guide unit 81 has the distal end light-projecting portion 91 fixed to the distal end hard portion 71 of the distal end portion 39 of the endoscope insertion part 25. Additionally, the first protective tube 93A and the second protective tube 93B are inserted through a plurality of joint rings 111 arranged in the curvable portion 37, and reach the soft portion 35. Although the details will be described below, a manipulating wire (not shown) is pulled by the manipulation of the angle knobs 33 (refer to FIG. 2) by an operator, and a plurality of joint rings 111 is turned about coupling shafts 113 and 115 by the pulling of this manipulating wire.

As the above arrangement is adopted, and the first protective tube 93A covers at least the optical fiber 55 in the range of the curvable portion 37, when the curvable portion 37 is curved, the first protective tube 93A deforms flexibly and absorbs the pressure from a tube lateral face applied to the optical fiber 55. As a result, the buckling of the optical fiber 55 covered with the first protective tube 93 can is prevented, and occurrence of disconnection can be inhibited. Additionally, since the first protective tube 93A has high flexibility even when the first protective tube is curved in the curvable portion 37, and abuts on and rubs against other built-in components, other built-in components are not damaged. There is no level difference on the outer surface of the light guide unit 81 in the region of a curvable portion 37, and this also does not damage other built-in components. Additionally, since there is no level difference, slidability to other built-in components also improves.

Since the first protective tube 93A is formed of a material with a small elastic constant, the first protective tube is apt to bend. Therefore, the resistance against curving operation is little, the manipulation force of turning the angle knobs 33 shown in FIG. 2 is small, and the manipulability of the endoscope improves.

As shown in FIG. 8, the soft portion 35 is adapted to cover a coil 117 with a tube 119. The coil 117 is fixed at a connection place 123 between the soft portion 35 and the curvable portion 37 by a fixing member 121. Therefore, since the fixing member 121 is arranged, the internal diameter of the connection place 123 is relatively small.

Thus, if the first protective tube 93A is provided to extend into the region of the soft portion 35 where the connection place 123 is avoided, and is connected to the connecting member 103 at a position where the first protective tube is inserted into the soft portion 35, degradation of slidability caused by interference with a smaller-diameter portion of the connection place 123 or degradation of the curving manipulability of the curvable portion 37 can be prevented. That is, the light guide unit 81 can smoothly slide without being caught in the fixing member 121 of the connection place 123, and degradation of flexibility caused by the presence of the connecting member 103 does not reach the curvable portion 37.

Figure 9A:
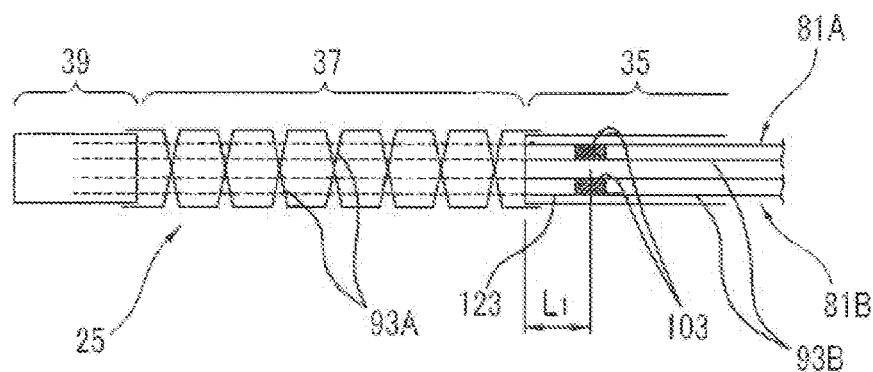
FIGS. 9A and 9B—FIG. 9A is a schematic explanatory view showing a configuration in which a connection part between a first protective tube and a second protective tube is provided at a soft portion when a plurality of light guide units is built in the endoscope insertion part.

Additionally, as shown in FIG. 9A, even when a plurality of light guide units 81A and 81B are built in the endoscope insertion part 25, the connecting member 103 interposed between the first protective tube 93 and the second protective tube 93B is provided at an axial position shifted into the soft portion 35 by a distance L1 from the end of the soft portion 35 on the side of the curvable portion 37 in such a manner to avoid the connection place 123. This can prevent degradation of the slidability of the light guide units 81A and 81B or degradation of the curving manipulability of the curvable portion 37.

Figure 9B:
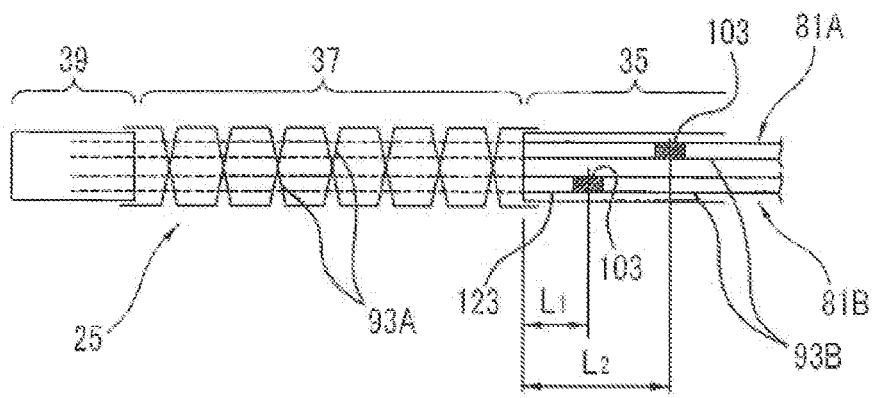

Moreover, as shown in FIG. 9B, the same effects as above are obtained by providing the connecting member 103 that becomes the connection part between the first protective tube 93A and the second protective tube 93B at an axial position different for each of the light guide units 81A and 81B. Additionally, occurrence of a bias in the curving stiffness of the soft portion 35 caused by overlap of the connecting members 103 of the respective protective tubes 93A and 93B can be prevented.

The protective tube 93 has a surface friction coefficient of the second region 93B smaller than the surface friction coefficient of the first region 93A. This can makes the slidability of the second protective tube 93B, which is longer than the first protective tube 93A, excellent over its entire length. Hence, the workability when the optical fiber 55 is inserted through the tube improves, and entanglement in other built-in components in the soft portion can be made difficult.

Next, the effects caused by covering an optical fiber in the region of the curvable portion 37 with the first protective tube 93A will be further described.

Figure 10:
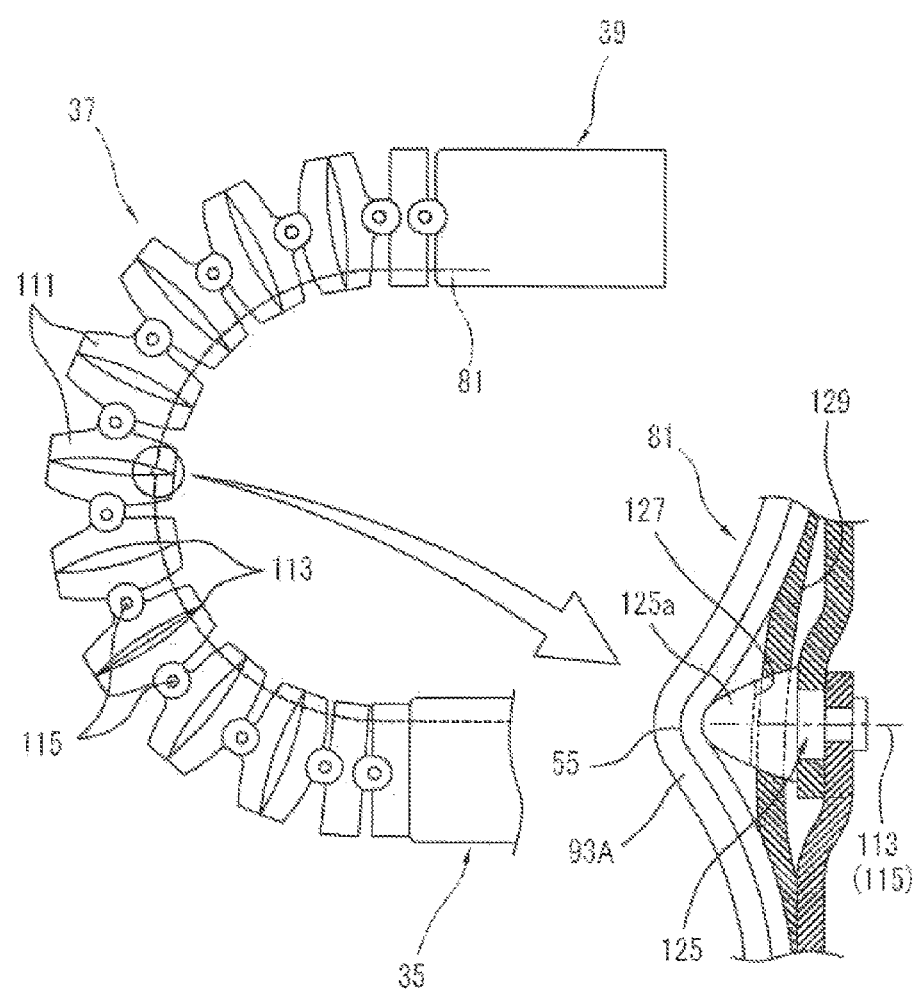
FIG. 10 is a schematic explanatory view showing a case where bending has occurred in a portion of the light guide unit when a curvable portion is curved.

FIG. 10 is a schematic explanatory view showing a case where bending has occurred in a portion of the light guide unit when a curvable portion is curved. In the curvable portion 37 formed between the distal end portion 39 and the soft portion 35, the plurality of joint rings 111 mentioned above are coupled together about the coupling shafts 113 and 115, respectively, that are turnable to each other. The plurality of joint rings 111 can be curved in a desired direction by the pulling of the manipulating wire by the manipulation of an angle knob.

A pivot pin 125 is arranged in the coupling shaft 113 (115 is the same), which couples the adjacent joint rings 111 together, to couple both the joint rings 111 turnably. A through hole 127 is formed in a head 125a of the pivot pin 125 that protrudes toward the center of the joint ring 111, and the manipulating wire 129 is inserted through the through hole 127.

Various kinds of built-in components including the light guide unit 81 are received inside the joint rings 111, and the respective built-in components are also curbed along the curvable portion 37 with the curving operation of the curvable portion 37. In that case, the protruding head 125a of the pivot pin 125 may be pressed against the first protective tube 93A of the light guide unit 81, and the first protective tube 93A may be bent with a small curvature radius. Bending generated in the first protective tube 93A induces disconnection of the optical fiber 55 inserted through the tube.

Figure 11:
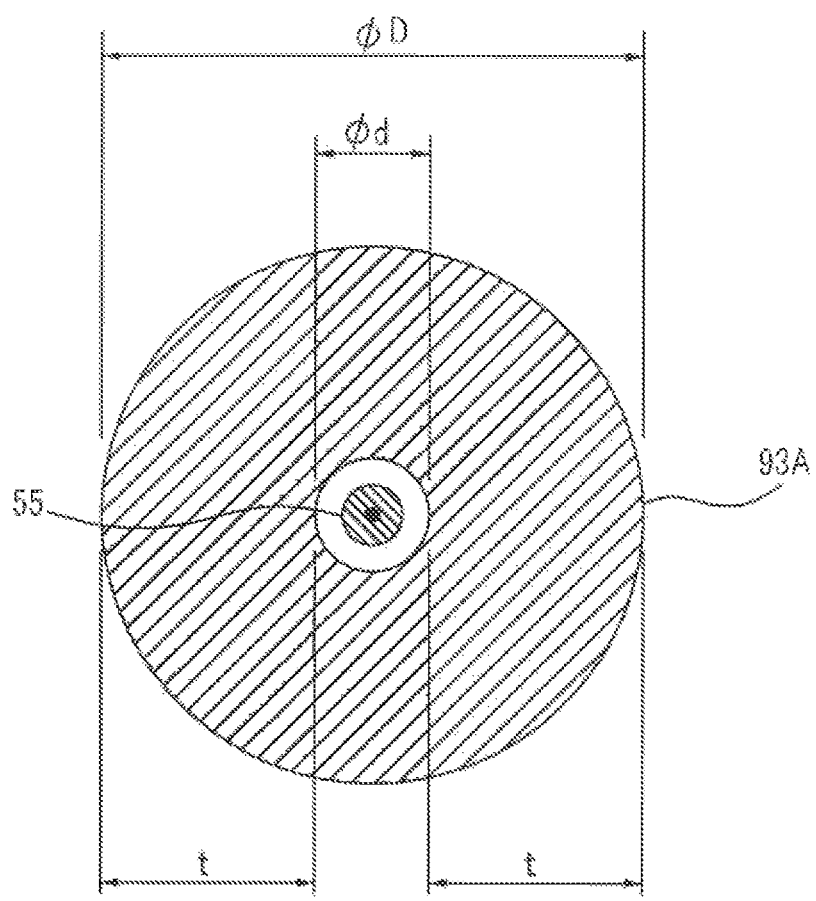
FIG. 11 is a cross-sectional view of the first protective tube.
Figure 12:
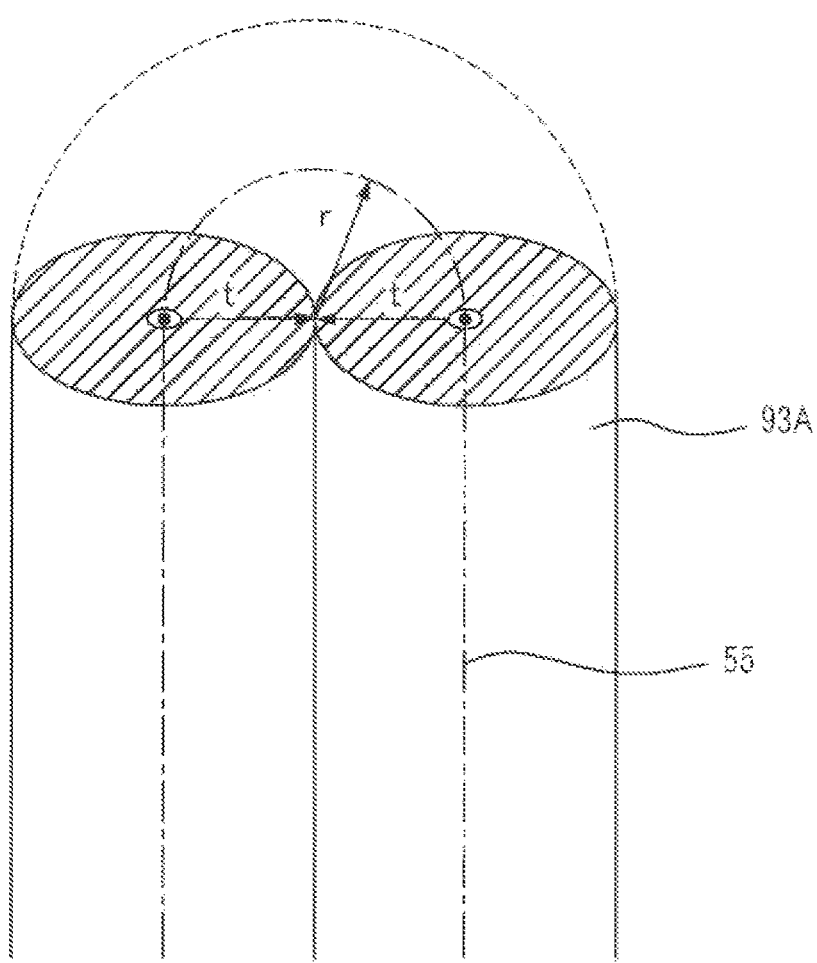
FIG. 12 is an explanatory view showing a state where the first proactive tube is bent at 180°.

However, in the first protective tube 93A of the present configuration, as previously described, the thickness t that can be found as ½ of the difference between the external diameter D and the internal diameter d is made larger than the greatest curvature radius $r_{max}$ at which the optical fiber 55 breaks due to bending as shown in the cross-sectional view of the first protective tube 93A in FIG. 11. Thereby, even when the protective tube 93A is bent at 180° as shown in FIG. 12, and is bent with a minimum curvature radius, the curvature radius r of the optical fiber 55 becomes always larger than the curvature radius $r_{max}$ at which breaking occurs. Accordingly, according to this configuration, disconnection does not occur in the optical fiber 55 by any manipulations of the curvable portion 37.

As described above, the present invention is not limited to the above embodiment. Changing or applying the present invention by those skilled in the art on the basis of the description of the specification, or well-known techniques are scheduled by the present invention and is included within a range where protection is required. For example, although the protective tube is provided to cover the outside of the optical fiber 55 in this configuration example, the protective tube may cover not only the optical fiber 55, but also other built-in components, such as the forceps tube 79, the air supply and water supply tube 89, and the signal cable 51 shown in FIG. 6. Additionally, the global elastic constant (bending stiffness) of the protective tube may be made different by making the shapes of the first region and the second region different from each other in addition to changing the elastic constant by selection of materials. Additionally, the protective tube may be a tube made by two-color molding or insert molding of materials with different elastic constants in addition to the configuration in which a plurality of tube members are coupled together. Thereby, the connecting member 103 becomes unnecessary, reliability improves, and maintenance becomes easy.

As described above, the following matters are disclosed in the present specification.

(1) An endoscope including a curvable portion provided to extend at a distal end of a soft portion having flexibility, and elongated insertion part to be inserted into a subject, an elongated flexible body built in the insertion part, and a protective tube that covers an outer periphery of the flexible body, the protective tube having a first region that covers the flexible body located at least in the curvable portion, and a second region that covers the flexible body located in the soft portion, and the elastic constant of the first region being smaller than the elastic constant of the second region, and the external diameter of the protective tube in the first region being larger than the external diameter of the protective tube of the second region.

According to this endoscope, there is provided an endoscope in which the elastic constant of the first region of the protective tube is set to a value smaller than the elastic constant of the second region, and the external diameter of the protective tube in the first region is made larger than the external diameter of the protective tube of the second region. Thereby, when the curvable portion is curved, the first region deforms flexibly at a radius that is equal to or more than the greatest radius of rotation at which the flexible body breaks, so that the pressure from the lateral face applied to the flexible body can be absorbed. As a result, the flexible body can be prevented from buckling. Additionally, even if the first region of the protective tube is curved in the curvable portion and abuts on other built-in components, since the first region has high flexibility, other built-in components are not damaged. Moreover, as the first region with a small elastic constant is arranged at least in the region of the curvable portion, resistance against the curving operation of the curvable portion decreases and curving manipulability improves.

(2) The endoscope of (1) in which the first region and the second region are made of different materials, respectively.

According to this endoscope, the elastic constant can be simply made different by forming the first region and second region of the protective tube of different materials, respectively.

(3) The endoscope of (2) in which the first region is made of a rubber based material.

According to this endoscope, the rubber-based material is applied to the first region, so that flexibility is enhanced and the flexible body can be protected from the pressure from a lateral face. Additionally, the flexible body can be maintained in a straight shape by an elastic restoring force, and assemblability when the flexible body is inserted into the insertion part improves.

(4) The endoscope of (2) in which the first region is provided by performing fluorine-based coating on the surface of the rubber-based material.

According to this endoscope, the fluorine-based coating is performed on the surface of the rubber-based material, so that slidability with the flexible body inserted into the inner surface of the first region, or other built-in components that touch the outer surface becomes good, and the curving manipulability or assemblability of the curvable portion can be improved.

(5) The endoscope of (3) or (4) in which the rubber-based material includes either silicone rubber or fluorine-based rubber.

According to this endoscope, a rubber material that has high flexibility and is chemically stable is used for the first region, so that the rubber material does not alter even if the endoscope is touched by cleaning chemicals when being washed, and also has little degradation with time.

(6) The endoscope of any one of (2) to (5) in which the second region of the protective tubs is made of a fluorine-based resin material.

According to this endoscope, the fluorine-based resin material is applied to the second region, so that slidability with the flexible body inserted into the inner surface of the second region, or other built-in components that touch the outer surface becomes good, and assemblability of the soft portion improve.

(7) The endoscope of (6) in which the fluorine-based resin material includes either polytetrafluoroethylene (PTFE) or a tetrafluoroethylene perfluoroalkyl vinyl ether copolymer (PEA).

According to this endoscope, high slidability can be obtained in the second region of the protective tube.

(8) The endoscope of any one of (1) to (7) in which the tensile modulus of the first region is in the range of 5 to 50 MPa, and the tensile modulus of the second region is in the range of 100 to 600 MPa.

According to this endoscope, the assemblability of the endoscope and the curving manipulability of the curvable portion can be sufficiently secured.

(9) The endoscope of any one of (1) to (8) in which the tensile modulus of the second region is 2 to 20 times larger than the tensile modulus of the first region.

According to this endoscope, the assemblability of the endoscope and the curving manipulability of the curvable portion can be sufficiently secured.

(10) The endoscope according to any one of (1) to (9) in which the first region and of the second region of the protective tube are constituted by separate tube members, respectively, and a connection part of the tube member between the first region and the second region is arranged in the soft portion.

According to this endoscope, the connection part of the tube member is arranged in the soft portion, so that degradation of slidability in the curvable portion or degradation of the curving manipulability of the curvable portion can be prevented.

(11) The endoscope of (10) in which a plurality of the flexible bodies covered with the protective tube is arranged inside the insertion part, and the connection part between the first region and the second region of the protective tube is arranged at an axially different position for each of the protective tubes.

According to this endoscope, a bias can be prevented from occurring in the curving stiffness of the soft portion due to overlap of the connection parts of the respective protective tubes.

(12) The endoscope of any one of (1) to (12) in which surface friction coefficient of the second region of the protective tube is smaller than the surface friction coefficient of the first region.

According to this endoscope, the slidability in the second region of the protective tube becomes good, the workability when the flexible body is inserted into the tube can be improved, and the slidability between other built-in components in the soft portion and the protective tabs can be improved.

(13) The endoscope of any one of (1) to (12) in which the flexible body is an optical fiber that transmits illumination light to the distal end of the insertion part.

According to this endoscope, disconnection of an optical fiber can be prevented.

What is claimed is:

1. An endoscope comprising:
   an insertion part including a distal end portion, a curvable portion connected to the distal end portion, and a soft portion connected to the curvable portion, and
   a body manipulating part connected to the soft portion,
   wherein the soft portion has a flexibility and the curvable portion is curvable by manipulating the body manipulating part,
   the endoscope further comprising,
   a first light guide unit arranged inside the curvable portion and the soft portion, and fixed to the distal end portion,
   a second light guide unit arranged inside the curvable portion and the sofa portion, and fixed to the distal end portion,
   wherein the first light guide unit has a first region extended from inside of the curvable portion to the inside of the soft portion, and a second region located at the body manipulating part side with respect to the first region and inside the soft portion,
   the second light guide unit has a third region extended from inside of the curvable portion to the inside of the soft portion, and a fourth region located at the body manipulating part side with respect to the third region and inside the soft portion,
   an proximal end portion of the third region inside the soft portion is located at a different position along an axial direction of the insertion part with respect to an proximal end portion of the first region inside the soft portion,
   an external diameter of the first region is larger than an external diameter of the second region,
   an external diameter of the first light guide unit decreases in a stepwise manner from the first region to the second region,
   an external diameter of the third region is larger than an external diameter of the fourth region, and
   an external diameter of the second light guide unit decreases in a stepwise manner from the third region to the fourth region.

2. The endoscope according to claim 1,
wherein the proximal end portion of the third region inside the soft portion is located at the body manipulating part side with respect to the proximal end portion of the first region inside the soft portion.

* * * * *